United States Patent [19]

Holleboom

[11] Patent Number: 5,139,639
[45] Date of Patent: Aug. 18, 1992

[54] ELECTROCHEMICAL TYPE EXHAUST GAS OXYGEN SENSOR

[75] Inventor: Bruce W. Holleboom, Grand Blanc, Mich.

[73] Assignee: General Motors Corporation, Detroit, Mich.

[21] Appl. No.: 666,318

[22] Filed: Mar. 8, 1991

[51] Int. Cl.⁵ .................................... G01N 27/417
[52] U.S. Cl. .................................. 204/427; 204/424
[58] Field of Search ............... 204/424, 427, 428, 429

[56] References Cited

U.S. PATENT DOCUMENTS

| | | | |
|---|---|---|---|
| 3,844,920 | 10/1974 | Burgett et al. | 204/195 S |
| 4,076,608 | 2/1978 | Fujishiro et al. | 204/427 |
| 4,220,516 | 9/1980 | Sano et al. | 204/427 X |
| 4,222,840 | 9/1980 | Murphy et al. | 204/427 X |
| 4,609,454 | 9/1986 | Ziegler | 204/427 |
| 4,824,550 | 4/1989 | Ket et al. | 204/427 |

*Primary Examiner*—John Niebling
*Assistant Examiner*—William T. Leader
*Attorney, Agent, or Firm*—Cary W. Brooks

[57] ABSTRACT

This invention provides a solid electrolyte, electrochemical-type oxygen sensing device which is suitable for detecting oxygen partial pressures of exhaust gases emitted from an internal combustion engine. The oxygen sensing device of this invention has a novel self-aligning fixturing means for rigidly securing, sealing, and electrically contacting the solid electrolyte body within the sensor assembly. The electrically conductive fixturing means also electrically communicates the galvanic output signal generated between the reference and measuring electrodes provided on the solid electrolyte body to an external electrical connector. The fixturing means is a substantially tubular body having an outwardly flared region which is contiguous with an inwardly tapered end. The inwardly tapered end is matched to the inner diameter of the open end of the solid electrolyte body.

6 Claims, 2 Drawing Sheets

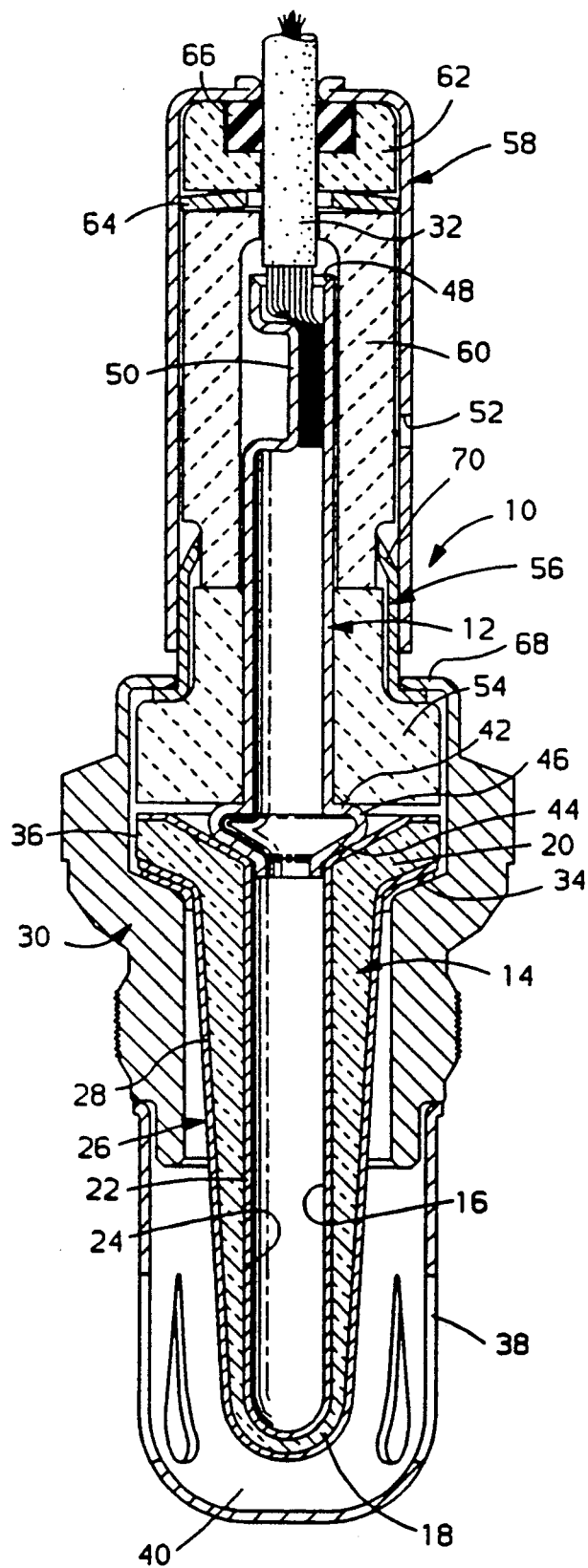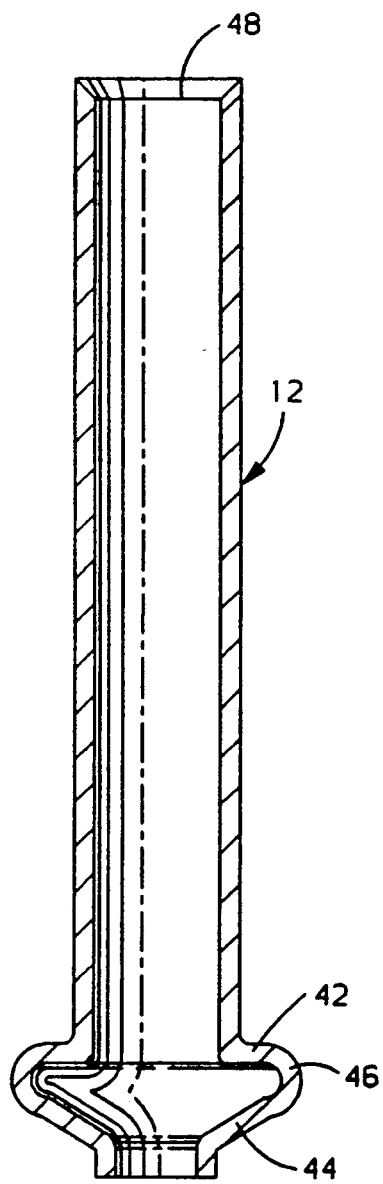
FIG. 1
FIG. 2

ELECTROCHEMICAL TYPE EXHAUST GAS OXYGEN SENSOR

The present invention to an electrochemical type solid electrolyte oxygen sensor suitable for detecting oxygen concentrations in automotive exhaust emitted from an internal combustion engine. More specifically, this invention relates to an oxygen sensor of this type which is rugged, durable and readily assembleable.

BACKGROUND OF THE INVENTION

Gas sensors are employed in a variety of applications requiring qualitative and quantitative gaseous determinations. In the automotive industry, it is well known that the oxygen concentration in the automobile exhaust has a direct relationship to the engine air-to-fuel ratio. Oxygen gas sensors are employed within the automobile internal combustion control system to provide accurate exhaust gas oxygen concentration measurements for determination of optimum combustion conditions, maximization of efficient fuel usage, and management of exhaust emissions.

Generally, the electrochemical type of oxygen sensor employed in automotive applications utilizes a thimble shaped electrochemical galvanic cell to determine, or sense the relative amounts of oxygen present in the exhaust stream, an example being U.S. Pat. No. 3,844,920 to Burgett et al. This type of oxygen sensor is generally known and used throughout the automotive industry, and comprises an ionically conductive solid electrolyte material which is typically yttria stabilized zirconia, a porous electrode coating on the exterior of the solid electrolyte exposed to the exhaust or measuring gas, and a porous electrode coating on the interior of the solid electrolyte exposed to a known concentration of reference gas.

The gas concentration gradient across the solid electrolyte produces a galvanic potential which is related to the differential of the partial pressures of the gas at the two electrodes by the Nernst equation: $E = AT \ln[P_1/P_2]$, where E is the galvanic voltage, T is the absolute temperature of the gas, $P_1/P_2$ is the ratio of the partial pressures of the reference gas at the two electrodes, and $A = R/4F$, where R is the universal gas constant and F is the Faraday constant Thus, the oxygen sensing device determines the oxygen concentration in the exhaust gas, by measuring this galvanic potential generated between the reference and measuring electrodes.

Two extremely important functional requirements of an automotive exhaust oxygen sensor are (1) the ability of the sensor assembly to maintain electrical contact between the measuring and reference electrodes and the external measuring equipment, while (2) preventing leakage of the exhaust gases into the air reference chamber (and correspondingly to the reference electrode) of the solid electrolyte body. It is also required that these functions be strictly maintained over a wide range of temperatures with materials having diverse thermal expansion characteristics.

Various means have been employed in the past to achieve good sealing and electrical contact within the sensor assembly over a wide range of temperatures. Most of these means utilize some type of spring member to achieve the requisite gas-tight seal and electrical contact, and can generally be divided into two broad categories, In the first category, the spring member is placed inside the gas sensor shell near the region where the hot exhaust gases flow, typically between an insulator and the positive electrical contact on the solid electrolyte body. This design requires a spring material which can tolerate the high temperatures experienced as the exhaust gases flow over the solid electrolyte body. Such materials are relatively expensive and do not provide optimum spring properties In addition, typically, such an arrangement subjects the spring member to extremely high loading forces during assembly of the components, resulting in a significant loss in its spring force.

Alternatively, the spring member has been provided away from the extremely hot section of the sensor assembly where the exhaust gases flow. However, although this design permits the use of less costly materials for the spring member, it is still required that the full assembly force be applied to the spring member, thereby again diminishing the spring force of the member.

Therefore, it would be desirable to provide a means for assembling these types of oxygen sensors which does not employ a spring member to ensure effective sealing and electrical contact within the sensor.

A significant, additional drawback also exists with regard to the use of either of these typical arrangements for achieving adequate sealing and electrical contact In order to functionally test the assembly, the typical design requires the assembly of the entire sensor, including the wiring and incorporation of all metal components. This is problematic since the wiring adds complexity to the high volume automatic testing of these assemblies. In addition, it is extremely difficult to salvage some of the components if a defect is detected at such an advanced stage in the assembly of the exhaust oxygen sensor.

Therefore, it would also be desirable to provide a means for assembling these automotive exhaust oxygen sensors which would permit the testing of a functional subassembly prior to final build-up of the sensor assembly, thereby maximizing the amount of salvageable material upon detection of a defect. Further, for automotive applications particularly, it is required that the oxygen sensor be rugged, reliable, and readily manufacturable at a low cost, therefore accordingly the assembly means should be amenable to these production requirements.

SUMMARY OF THE INVENTION

It is an object of this invention to provide an improved solid electrolyte electrochemical-type oxygen sensor, the improved oxygen sensor being durable and reliable in operation even in comparatively varying environmental conditions.

It is a further object of this invention that such an improved oxygen sensor have a self-aligning means for rigidly securing and thereby sealing the solid electrolyte body within the sensor assembly, such means also electrically coupling the appropriate electrodes on the solid electrolyte body to external electronic equipment.

It is still a further object of this invention that such an improved oxygen sensor be readily adaptable to automotive production and testing techniques.

In accordance with a preferred embodiment of this invention, these and other objects and advantages are accomplished as follows.

According to the present invention, there is provided an oxygen sensing device suitable for detecting oxygen concentrations in automotive exhaust gases emitted from an internal combustion engine.

Generally, the oxygen sensing device has a substantially tubular solid electrolyte body, a housing and an electrically conductive fixturing means for securing the solid electrolyte body within the housing. The solid electrolyte body has an elongated bore located axially, with a first end closed by the solid electrolyte material and a second end open. A reference electrode is provided on the inner surface of the solid electrolyte body and a measuring electrode is provided on the outer surface. The housing supports the solid electrolyte body so that the measuring electrode of the solid electrolyte body contacts the external gas to be measured and so that the reference electrode is essentially gas tight to the external gas to be measured The oxygen partial pressure of the exhaust gas is determined by measuring the galvanic potential generated between the reference and measuring electrodes.

According to a preferred aspect of this invention, the electrically conductive fixturing means rigidly secures and centers the solid electrolyte body within the housing, while also electrically coupling the galvanic output signal generated between the reference electrode and the measuring electrode to the external electronic measuring equipment.

The fixturing means is substantially tubular and has an outwardly flared region which is contiguous with an inwardly tapered end. The inwardly tapered end provides a frusto-conical surface surrounding a lower tubular extension that seats on a complementary frusto-conical surface on the upper open end of the solid electrolyte body. The reference electrode extends up onto the frusto-conical surface of the solid electrolyte body. Hence, the frusto-conical lower end of the fixturing means securely contacts the reference electrode when inserted within the upper open end of the solid electrolyte body. During assembly of the sensor, the inwardly tapered end of the fixturing means is inserted within the open end of the solid electrolyte body, and thereby forces the solid electrolyte body downward against a gasket appropriately provided at the angled seat of the housing. The solid electrolyte body is rigidly held within the housing by the complementary frusto-conical fit generated near its inner diameter between itself and the fixturing means, and the complementary frusto-conical fit near its outer diameter between itself and the gasket. In addition, the compression fit between the gasket and housing effectively seals the sensor from entry of unwanted exhaust gases into its reference air chamber. With this preferred embodiment, the sensor is effectively secured and sealed.

An inventive feature of this invention is that the electrically conductive fixturing means is tapered so as to provide the fit between itself and the solid electrolyte body, while also providing appropriate electrical contact with the reference electrode on the inner diameter of the solid electrolyte body. In addition, the electrically conductive fixturing means electrically communicates the galvanic signal generated between the reference and measuring electrodes to external electronic equipment. In the preferred embodiment, the fixturing means is crimped sufficiently near the end opposite its inwardly tapered end, so as to retain an appropriate electrical connector after insertion of the electrical connector into its tubular body. The electrical connector then communicates the galvanic output signal generated between the reference and measuring electrodes to the desired external electronic measuring equipment.

Therefore, the electrically conductive fixturing means in accordance with this invention facilitates the rigid securing, sealing and centering of the solid electrolyte body within the sensor housing, while also electrically coupling the galvanic output signal generated between the reference and measuring electrodes to the external electrical connector. In addition, the preferred embodiment permits easy assembly of the oxygen sensor while also providing a testable subassembly so as to allow testing of the sensor prior to final build up of the device.

Other objects and advantages of this invention will be better appreciated from the following detailed description.

BRIEF DESCRIPTION OF THE DRAWINGS

FIG. 1 is a cross-sectional view of a solid electrolyte oxygen sensor in accordance with a preferred embodiment of this invention and illustrates the solid electrolyte body, housing and self-aligning fixturing means having an outwardly flared region contiguous with an inwardly tapered end.

FIG. 2 is a cross-sectional view of the fixturing means shown in FIG. 1 in accordance with a preferred embodiment of this invention.

DETAILED DESCRIPTION OF THE INVENTION

Figure 3:
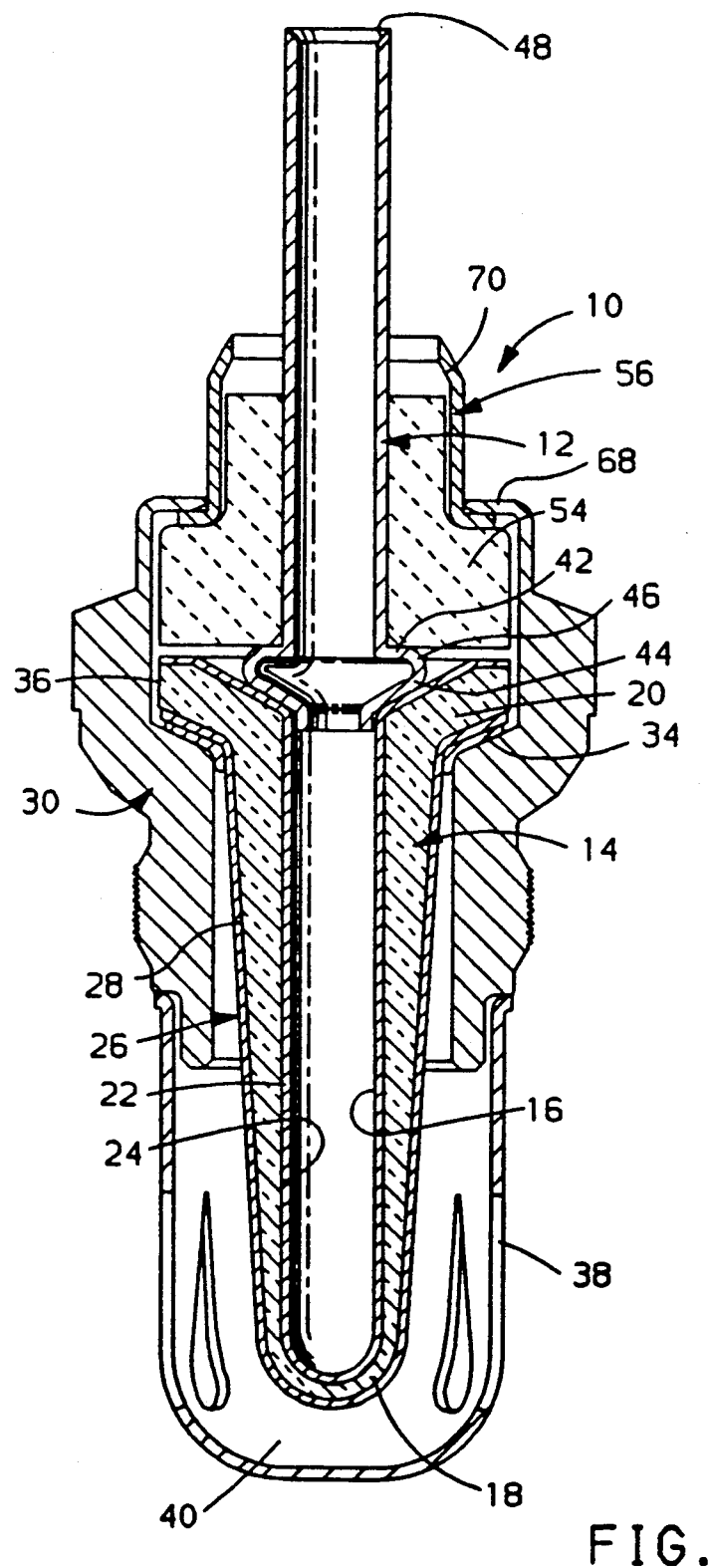
FIG. 3 is a cross-sectional view of a testable subassembly having the preferred fixturing means in accordance with this invention.

This invention provides a solid electrolyte, electrochemical-type oxygen sensing device which is suitable for detecting oxygen partial pressures of exhaust gases emitted from an internal combustion engine. The oxygen sensing device of this invention has a novel self-aligning fixturing means for rigidly securing, sealing, and electrically contacting the solid electrolyte body within the sensor assembly.

In the preferred embodiment of this invention, the oxygen sensing device 10, as shown cross-sectionally in FIG. 1, comprises the preferred self-aligning fixturing means 12 for securing the solid electrolyte body 14 within the housing 30 while also electrically coupling the signal generated between electrodes on the solid electrolyte body 14 to an external electrical connector 32. The oxygen sensing device 10 shown in FIG. 1 is approximately three times the size of an actual oxygen sensing device formed in accordance with this invention.

The solid electrolyte body 14 is preferably formed from yttria stabilized zirconia because of its good ionic and electronic conductivity, proven durability and availability, although other suitable electrically and ionically conductive materials may also be used. The solid electrolyte body 14 is substantially tubular having an elongated bore 16 located axially. The first end 18 of the solid electrolyte body 14 is closed by the solid electrolyte material. The second end 20 of the solid electrolyte body 14 is open.

A reference electrode 22 is provided on the inner surface 24 of the solid electrolyte body 14 in the elongated bore 16. The reference electrode 22 extends up onto the frusto-conical upper surface of the solid electrolyte body where it makes physical and electrical contact with the inwardly tapered end 44 of the self-aligning fixturing means 12. The reference electrode 22 is preferably formed from porous platinum because of its high surface area, good catalytic properties and relatively low cost as compared to the other noble metal catalyst materials, although other suitable electrically conductive surfaces may also be used such as porous gold or palladium. The reference electrode 22 contacts a known concentration of a reference gas. Air is generally always used as the reference gas since it is readily available and can be easily introduced into the elongated bore. Other gases may also be used, however extraordinary and impractical plumbing features would be required to introduce the gas into the elongated bore 16, so as to contact the reference electrode 22.

A measuring electrode 26, preferably also formed from the porous platinum for the same reasons, (however again other suitable electrically conductive, and preferably catalytic, surfaces may be used) is provided on the outer surface 28 of the solid electrolyte body 14 and contacts the exhaust gas for which the oxygen concentration is to be measured The oxygen partial pressure of the exhaust gas is measured conventionally by detecting the galvanic potential generated between the reference and measuring electrodes 22 and 26 respectively. It is to be noted that generally, the outer measuring electrode 26, or at least that portion which is exposed to the exhaust gases, is also covered by a thin layer of a protective coating (not shown), typically a porous ceramic material, to shield the measuring electrode 26 from foreign poisons or particles within the exhaust gas. In order to make electrical contact to the outer measuring electrode 26, the measuring electrode extends upwardly and contacts the electrically conductive metal gasket 34 which contacts the housing 30.

The housing 30 is adapted to fit into the exhaust pipe of the automobile, not shown, but this is typically accomplished by the use of simple mounting plates. The housing 30 may be formed from any suitable high strength, preferably corrosion resistant material, such as a suitable stainless steel. The housing 30 supports the solid electrolyte body 14 so that the measuring electrode 26 on the outer surface 28 of the solid electrolyte body 14 contacts the external exhaust gas to be measured, while keeping the reference electrode 22 on the inner surface 24 of the solid electrolyte body 14 gas tight to the external exhaust gas. The solid electrolyte body 14 is mounted so as to resemble a finger-like projection into the flow of exhaust gases. Only about half to one-third of the solid electrolyte body 14 projects outwardly and is exposed to the exhaust gases.

A lower gasket 34, provided at the inner, angled seat of the housing 30, seals the solid electrolyte body 14 in that region between the solid electrolyte body 14 and the housing 30 and prevents flow of the external exhaust gas into the elongated bore 16 of the solid electrolyte body 14 where the reference electrode 22 is provided.

A perforated shield 38 is also preferably attached to the housing 30 for protection of the solid electrolyte body 14 during assembly and use. A gap 40 is provided between the perforated shield 38 and solid electrolyte body 14 at the sensing region of the solid electrolyte body 14 to allow uninterrupted flow of the exhaust gases through the perforated shield 38 to the porous platinum measuring electrode 26 on the outer surface 28 of the solid electrolyte body 14.

Shown cross-sectionally in FIG. 2 is the electrically conductive fixturing means 12 in accordance with the preferred embodiment of this invention. The electrically conductive fixturing means 12 rigidly secures, centers and seals the solid electrolyte body 14 within the housing 30, while also electrically coupling the galvanic output signal generated between the reference electrode 22 and the measuring electrode 26 to the external electronic signal wire 32. The fixturing means also provides means for maintaining the above-mentioned seal during thermal cycling.

The fixturing means 12 is substantially tubular and has an outwardly flared region 42 which is contiguous with an inwardly tapered end 44. The fixturing means 12 is formed from a suitable electrically conductive material. Preferably, the fixturing means 12 is formed from a stainless steel, such as an appropriate 400 series stainless steel, because of its electrical conductivity, high strength, and good corrosion resistance, however other electrically conductive, strong materials may also be used. The corrosion resistance is desirable since the sensor is exposed to the hot, corrosive internal combustion engine exhaust gases, which may reach temperatures as high as about 500° C. The fixturing means 12 is formed by appropriately drawing the tubular structure from the desired material or by other conventional forming techniques.

The diameter of the outwardly flared region 42 of the fixturing means 12 is approximately twice the tubular diameter of the fixturing means 12 as measured essentially along its entire length. The outwardly flared region 42, as shown is essentially perpendicular to the tubular structure of the fixturing means 12. It is imperative that this outwardly flared region 42 be substantially flat and perpendicular to the tubular fixturing means structure 12, for alignment purposes during assembly of the sensor 10. The flat surface of the outwardly flared region 42 provides a seat for a subsequently inserted component. Also, for purposes of better describing the invention, the drawings show a relatively squared corner between the tubular structure and the outwardly flared region 42. In practice there is a slight radius at this corner so as to minimize the stresses arising at this corner and because of the conventional forming techniques used.

Contiguous with the outwardly flared region 42 is an inwardly tapered end 44. In order to form this inwardly tapered end 44, an arcuate region 46 having a bending angle of about 150°–170° is required. The angle of this arcuate region 46 will be determined by the taper of the inwardly tapered region 44 of the fixturing means 12, discussed later Care must be taken during forming of this arcuate region 46 so that the material is not overly strained or thinned Appropriate heat treating of this part may also be necessary after forming so as to relieve any unwanted strains generated during the forming of this part.

The inwardly tapered end 44 is drawn to a tapered angle which matches the tapered angle at the open end 20 of the solid electrolyte body 14 (shown more clearly in FIG. 1). The angle of the tapered end 44 of the fixturing means 12 is approximately 30° as measured with respect to the outwardly flared region 42. The degree of taper depends upon the degree of taper of the open end 20 of the solid electrolyte body 14, and depends upon many factors. The foremost considerations for determining the degree of taper are (1) that there be matched, mating surfaces between the open end 20 of the solid electrolyte body 14 and the inwardly tapered end 44 of the fixturing means 12 so as to ensure thorough sealing between the two components to prevent any leakage of exhaust gases into the elongated bore 16 of the solid electrolyte body 14, and (2) that the two surfaces contact sufficiently to provide electrical contact between the electrically conductive fixturing means 12 and the reference electrode 22 on the interior of the solid electrolyte body.

Certainly, it is not desirable to make the degree of taper too acute, since that would unduly stress the components during assembly and use and may not provide adequate contact between the end 44 of the fixturing means 12 and the open end 20 of the solid electrolyte body 14. (Although it is foreseeable that if the open end 20 of the solid electrolyte body 14 were appropriately flattened, a fixturing means 12 having only the flattened outwardly flared region 42 could also be used.) However, with the embodiment shown, nor would a degree of taper which is too large, wherein it is approaching almost perpendicularity with the outwardly flared region 42 be satisfactory, since that would require the fixturing means 12 to become too long with a possible decrease in its ability to rigidly secure, seal and center the solid electrolyte body 14. An acute angle of taper of about 30° (with respect to the outwardly flared region 42 as shown) is preferred since it appears to optimize these concerns while also still being relatively easily to machine and form. It is foreseeable that the fixturing means 12 could have an angle of taper ranging between about 20° to about 45° so as to perform satisfactorily, and even an angle of taper of up to about 60°, without detrimental results to the function of the oxygen sensor 30 or to the advantages of this invention.

The inwardly tapered end 44 is matched to the open end 20 of the solid electrolyte body, so as to securely seal the open end 20 from external exhaust gases, and so as to contact the interior reference electrode 22 of the solid electrolyte body 14 when inserted within the solid electrolyte body 14. The inwardly tapered end 44 can either narrow or enlarge the diameter of the fixturing means 12 since it depends upon the size of the inner diameter of the elongated bore 16 of the solid electrolyte body 14 and may vary according to the particular application As shown in the accompanying figures, the inwardly tapered end 44 of the fixturing means 12 has at its extreme end a slight male portion which is again parallel with the tubular structure of the fixturing means 12, so as to securely lock into and align with the inner diameter of the solid electrolyte body 14. Again it is repeated that the mating angles between the inwardly tapered end 44 of the fixturing means 12 and the open end 20 of the solid electrolyte body 14 must be chosen carefully so as to ensure mating surfaces and will generally be within the preferred range above specified, so as to prevent excessive tensional stress when the fixturing means 12 is inserted within the solid electrolyte body 14.

During assembly of the sensor 10, the inwardly tapered end 44 of the fixturing means 12 is inserted within the open end 20 of the solid electrolyte body 14, and rigidly retains the solid electrolyte body 14 downwardly against the angled seat of the housing 30 where gasket 34 is provided The solid electrolyte body 14 is firmly held within the housing 30 by compression between fixturing means (at the solid electrolyte inner diameter) and the angled seat of housing 30, through gasket 34 (at the solid electrolyte outer diameter 36). The fixturing means 12 thereby provides a means for firmly securing the solid electrolyte body 14 within the housing 30 while also maintaining a continuous seal for the interior of the solid electrolyte body 14 at its open end 20 from the exhaust gases. During assembly, the fixturing means 12 also assists in the alignment and centering of the solid electrolyte body 14 within the housing 30.

The electrically conductive fixturing means 12 also electrically communicates the galvanic signal generated between the reference and measuring electrodes 22 and 26 to external electronic measuring equipment. In the preferred embodiment, the fixturing means 12 is crimped 50 sufficiently near the end 48 opposite its inwardly tapered end 44, after insertion of an appropriate electrical connector 32, so as to securely retain and ensure electrical contact with the electrical connector 32. The term "crimped" is used to describe this region 50 of the fixturing means 12 wherein the tubular diameter is sufficiently narrowed, however any conventional means may be used for forming this sufficiently narrower diameter in the fixturing means 12. As shown, it is necessary that the diameter of the fixturing means 12 be narrowed by as much as about 75% so as to ensure adequate retention of the electrical connector 32. It is also foreseeable that a fixturing means 12 could be provided which would not require this crimped region 50 if the electrical connector were appropriately designed. The electrical connector 32 then communicates the galvanic output signal generated between the reference and measuring electrodes 22 and 26 to the desired external electronic measuring equipment (not shown).

An advantageous feature of this preferred fixturing means 12 is that it permits easy assembling of the sensing device 10 while also providing a testable subassembly before final build-up of the sensor 10. The testable subassembly is shown in FIG. 3. After insertion of the fixturing means 12 within the open end 20 of the solid electrolyte body 14, a dielectric insulator 54 is positioned around the fixturing means 12. Preferably, the insulator 54 is formed from alumina because of its physical characteristics and practical considerations, although other suitable dielectric materials may also be used. The alumina insulator 54 insulates the electrically conductive fixturing means 12 from the housing 30 and the subsequently inserted inner upper shield 56. The inner upper shield 56 facilitates later assembly of the sensing device 10 and is also preferably formed from a metal for its strength and durability during assembly and use. Therefore, the galvanic output signal generated between the reference and measuring electrodes 22 and 26, flows directly through the electrically conductive fixturing means 12 and into the electrical signal wire 32 without electrical shorting into the housing 30 or inner upper shield 56.

After assembly of these components as shown in FIG. 3, the housing 30 is sufficiently crimped or rolled inwardly at its top end 68 to rigidly secure the components in place. The top end 70 of the inner upper shield 56 has an inward taper or other such conformation to facilitate and align subsequent assembly of the sensor components. As shown in FIGS. 1 or 3, the preferred fixturing means 12 of this invention facilitates the rigid retention of the functional components of the sensor 10.

In addition, there is a clearance fit between the insulator 54 and the solid electrolyte body 14, and the side regions of the solid electrolyte body 14 and the housing 30, so as to compensate for the various differences in thermal expansion rates of the ceramic and metal materials. Another advantageous feature of this invention is that by its thin walled design, the inwardly tapered end 44 of the fixturing means 12 provides some stress relief during use from the thermally induced stresses which may arise.

This testable subassembly as shown cross-sectionally in FIG. 3 is crimped together to ensure rigid retention of the components using conventional assembly techniques. High pressures can be applied to rigidly secure the components since the materials and components within this subassembly are designed to handle these high loads and because there are no undesirable spring members employed in this subassembly. The subassembly is secure enough at this point to permit functional testing of the principal components, particularly the solid electrolyte body 14 of the sensor 10. This is a particularly advantageous feature of the fixturing means 12 of this invention, since early testing translates into reduced amounts and costs of scrapped material.

Further, the fixturing means 12 alleviates the previous requirement for a spring member and thereby facilitates the assembly of these components while also providing a sufficiently secure subassembly for functional testing.

Final assembly of the oxygen sensing device 10 as shown in FIG. 1 is as follows. The electrical signal connector 32 is inserted within the fixturing means 12 and the fixturing means 12 appropriately crimped around that region 50 so as to securely contact and retain the electrical connector 32. As shown in FIG. 1, the electrical connector 32 is enveloped by a conventional electrically insulative covering, probably a plastic of sorts, everywhere except within the fixturing means 12, wherein the metal connector is depicted.

An intermediate dielectric insulator 60, upper dielectric insulator 62, spring washer 64, dielectric cable seal 66, and outer upper shield 58 are all placed over the electrical signal connector 32 and fixturing means 12, as shown in FIG. 1. The intermediate and upper insulators 60 and 62 are preferably formed from the same dielectric material used in insulator 54, which is preferably alumina, so as to minimize the stresses arising during use due to mismatched thermal coefficients of expansion. The dielectric insulators 54, 60 and 62 surround the fixturing means 12 and electrical connector 32, and are necessary to prevent any detrimental electrical shorting between the metal components.

The upper dielectric insulator 62 is machined so as to hold a dielectric cable seal 66, which is preferably formed from a rubber or other elastic material so as to effect a thorough seal between itself 66 and the electrical connector 32. The cable seal 66 is held in compression to ensure a tight seal. Prior to assembly, the rubber cable seal 66 is relaxed to allow easy insertion of the electrical connector 32 into the rubber seal 66. It is only after the rubber cable seal 66 is inserted within the upper insulator 62 that it is compressed around the connector 32.

The spring washer 64 is located in the cool zone of the oxygen sensor 10 which is not directly exposed to the hot exhaust gas. The spring washer further ensures that a tight, secure fit between components is achieved. Because the spring washer 64 is located in the cool zone, it is possible during the material selection to optimize the desired characteristics for the spring washer 64. This is not always possible with previous oxygen sensor designs wherein the spring washers were employed at or near the hot regions of the sensor which were directly exposed to the exhaust gas, to sufficiently seal the interior bore of the solid electrolyte body. This is not necessary with the fixturing means 12 of this invention which provides an excellent seal between components.

After the electrical connector 32 has been attached to the fixturing means 12, the outer upper shield 58 is mated to the inner shield 56. Pressure is applied to establish a predetermined force on the spring washer 64 for optimum sensor 10 sealing. Once this force is achieved, the outer upper shield 58 is permanently attached to the inner shield 56 by welding, staking or other suitable technique.

Reference air is admitted into the sensor 10 typically through one or more holes 52 provided within the upper outer shield 58. Also, depending upon the application, if the inner shield 56 and outer upper shield 58 are not completely joined together, air may be introduced through the gaps between these shields 56 and 58. However, it is preferred that these shields 56 and 58 be completely joined using the welding techniques. If completely joined, the sensor 10 design is water-proof also, another advantageous feature of this invention.

There are many desirable features associated with this invention. The electrically conductive fixturing means is tapered so as to match the open 20 end of the solid electrolyte body 14, thereby providing the inner air reference seal required for the sensor 10, while also providing appropriate electrical contact with the reference electrode 22 on the inner diameter of the solid electrolyte body 14. Further, the solid electrolyte body 14 is held within the housing 30 and externally sealed by the downward force exerted by the electrically conductive fixturing means 12 upon insertion.

Therefore, the electrically conductive fixturing means in accordance with this invention facilitates the rigid sealing, securing and centering of the solid electrolyte body within the sensor housing, while also electrically coupling the galvanic output signal generated between the electrode and measuring electrodes to the external electrical connector. In addition, the preferred embodiment permits easy assembly of the oxygen sensor while also providing a testable subassembly so as to allow testing of the sensor prior to final build up of the device While our invention has been described in terms of a preferred embodiment, it is apparent that other forms could be adopted by one skilled in the art, such as by modifying the angles of the tapered end of the fixturing means, or by providing a flat end to mate with the open end of the solid electrolyte body, or even by modifying the region whereat the fixturing means contacts the electrical connector. Accordingly, the scope of our invention is to be limited only by the following claims.

The embodiments of the invention in which an exclusive property or privilege is claimed are defined as follows:

1. An oxygen sensing device, comprising:
 a substantially tubular solid electrolyte body having an elongated bore axially located, with a first end closed by said solid electrolyte and a second end open and having a tapered mouth, said solid electrolyte body having a reference electrode provided on an inner surface thereof and a measuring electrode provided on an outer surface thereof:
 a housing, said housing supporting said solid electrolyte body so that said measuring electrode of said solid electrolyte body contacts the external gas to be measured and so that said reference electrode of said solid electrolyte body is essentially gas tight to the external gas to be measured;

an electrically conductive member having first and second ends and constructed and arranged to rigidly secure said substantially tubular solid electrolyte body within said housing while also electrically coupling the galvanic output signal generated between said reference electrode and said measuring electrode to external electronic measuring equipment and to seal said open end of said tubular electrolyte body, said member being substantially tubular and having an outwardly flared portion forming a substantial flat shoulder being substantially perpendicular to the longitudinal axis of said member, said member having a tapered shoulder extending from the flat shoulder of said member to a male portion at said first end, said male portion being substantially parallel to the longitudinal axis of said member; and a tubular insulator having a bore formed therein for receiving at least a portion of said member extending toward said second end, said tubular insulator having a substantially flat shoulder at one end being substantially perpendicular to the longitudinal axis of said tubular insulator; said tubular insulator being biased so that a portion of said substantially flat shoulder of said insulator engages a portion of said substantial flat shoulder of said member and so that said tapered shoulder of said member engages a portion of said tapered mouth of the electrolyte body and said male portion extends into the bore of said electrolyte body.

2. An oxygen sensing device as recited in claim 1 wherein said solid electrolyte body is formed from yttria stabilized zirconia and said reference and measuring electrodes comprise platinum.

3. An oxygen sensing device, comprising:

a substantially tubular solid electrolyte body having an elongated bore axially located, with a first end closed by said solid electrolyte and a second end open and having a tapered mouth, said solid electrolyte body having a reference electrode provided on an inner surface thereof and a measuring electrode provided on an outer surface thereof;

a housing, said housing supporting said solid electrolyte body so that said measuring electrode of said solid electrolyte body contacts the external gas to be measured and so that said reference electrode of said solid electrolyte body is essentially gas tight to the external gas to be measured;

an electrical connector for communicating the galvanic output signal generated between said reference electrode and said measuring electrode to external electronic measuring equipment;

an electrically conductive member having first and second ends and constructed and arranged to rigidly secure said substantially tubular solid electrolyte body within said housing while also electrically coupling the galvanic output signal generated between said reference electrode and said measuring electrical to said electrical connector, said electrically conductive member being substantially tubular and having an outwardly flared portion which is contiguous with an inwardly tapered shoulder extending toward said first end, said inwardly tapered shoulder being constructed and arranged to seal said open end of said tubular electrolyte body, and said substantially tubular electrically conductive member having a portion of substantially narrower cross-sectional area adjacent to said second end, said electrical connector being retained and contacted at said portion of narrower cross-sectional area by said electrically conductive member;

said outwardly flared portion forming a substantial flat shoulder being substantially perpendicular to the longitudinal axis of said member, said tapered shoulder extending from the flat shoulder of said member to a male portion at said first end, said male portion being substantially parallel to the longitudinal axis of said member; and a tubular insulator having a bore formed therein for receiving at least a portion of said member extending toward said second end, said tubular insulator having a substantially flat shoulder at one end being substantially perpendicular to the longitudinal axis of said tubular insulator; said tubular insulator being biased so that a portion of said substantially flat shoulder of said insulator engages a portion of said substantial flat shoulder of said member and so that said tapered shoulder of said member engages a portion of said tapered mouth of the electrolyte body and said male portion extends into the bore of said electrolyte body.

4. An oxygen sensing device as recited in claim 3 wherein said solid electrolyte body is formed from yttria stabilized zirconia and said reference and measuring electrodes comprise platinum.

5. An oxygen sensing device comprising a substantially tubular solid electrolyte body with an elongated bore axially located, with a first end closed by said solid electrolyte and a second end open and having a tapered mouth, said solid electrolyte body having a reference electrode provided on an inner surface thereof and a measuring electrode provided on an outer surface thereof;

a housing, said housing supporting said solid electrolyte body so that said measuring electrode of said solid electrolyte body contacts the external gas to be measured and so that said reference electrode of said solid electrolyte body is essentially gas tight to the external gas to be measured;

an electrically conductive member having first and second ends and constructed and arranged to rigidly secure said substantially tubular solid electrolyte body within said housing while also electrically coupling the galvanic output signal generated between said reference electrode and said measuring electrode to external electronic measured equipment, said electrically conductive member being substantially tubular and having an outwardly flared portion forming a substantial flat shoulder being substantially perpendicular to the longitudinal axis of said member, said member having a tapered shoulder extending from the flat shoulder of said member to a male portion at said first end, said male portion being substantially parallel to the longitudinal axis of said member; and a tubular insulator having a bore formed therein for receiving at least a portion of said member extending toward said second end, said tubular insulator having a substantially flat shoulder at one end being substantially perpendicular to the longitudinal axis of said tubular insulator; said tubular insulator being biased so that a portion of said substantially flat shoulder of said insulator engages a portion of said substantial flat shoulder of said member and so that said tapered shoulder of said member engages a portion of said tapered mouth of the electrolyte body and said male portion extends into the bore of said electrolyte body.

6. An oxygen sensing device as recited in claim 5 wherein said solid electrolyte body is formed from yttria stabilized zirconia and said reference and measuring electrodes comprise platinum.

* * * * *